US00PP31129P2

(12) United States Plant Patent
Danziger

(10) Patent No.: US PP31,129 P2
(45) Date of Patent: Nov. 26, 2019

(54) ***LEUCANTHEMUM* PLANT NAMED 'DLEULUCGRC'**

(50) Latin Name: *Leucanthemum superbum*
Varietal Denomination: DLEULUCGRC

(71) Applicant: Gavriel Danziger, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 15/998,205

(22) Filed: Jul. 12, 2018

(51) Int. Cl.
*A01H 5/02* (2018.01)
*A01H 6/14* (2018.01)

(52) U.S. Cl.
USPC ..... Plt./285
CPC ..... *A01H 6/14* (2018.05)

(58) Field of Classification Search
USPC ..... Plt./285
See application file for complete search history.

*Primary Examiner* — Anne Marie Grunberg
(74) *Attorney, Agent, or Firm* — Cassandra Bright

(57) ABSTRACT

A new and distinct cultivar of *Leucanthemum superbum* plant named 'DLEULUCGRC' is disclosed, characterized by an upright, compact plant habit and single daisy flowers. Vernalization is not required. Plants exhibit good heat tolerance. The new variety is a *Leucanthemum* useful for ornamental garden and container uses.

2 Drawing Sheets

Latin name of the genus and species: *Leucanthemum superbum.*

Variety denomination: 'DLEULUCGRC'.

BACKGROUND OF THE INVENTION

The new cultivar is a product of a planned breeding program conducted by the inventor, Gavriel Danziger in Moshav Mishmar Hashiva, Israel. The objective of the breeding program was to produce new *Leucanthemum* varieties with good heat tolerance and not requiring vernalization. The open pollination resulting in this new variety was made during April of 2012.

Asexual reproduction of the new cultivar 'DLEULUCGRC' was first performed in March of 2014, by basal vegetative cuttings at a greenhouse in Moshav Mishmar Hashiva, Israel. All subsequent propagation has shown that the unique features of this cultivar are stable and reproduced true to type in successive generations.

SUMMARY OF THE INVENTION

The cultivar has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLEULUCGRC' These characteristics in combination distinguish 'DLEULUCGRC' as a new and distinct *Leucanthemum* cultivar:

1. Vernalization not required for flowering.
2. Good heat tolerance.

PARENT COMPARISON

Plants of the new cultivar 'DLEULUCGRC' are similar to plants of the parent variety, *Leucanthemum* 'LK-9-19' in most horticultural characteristics, however, plants of 'DLEULUCGRC' differ in the following ways:

1. 'DLEULUCGRC' begins flowering later than the seed parent variety.
2. 'DLEULUCGRC' is more heat tolerant than the seed parent.

COMMERCIAL COMPARISON

Plants of the new cultivar 'DLEULUCGRC' are similar to plants of the commercial variety *Leucanthemum* 'Snowcap', unpatented, in most horticultural characteristics. Plants of the new cultivar 'DLEULUCGRC', however, differ in the following:

1. 'DLEULUCGRC' does not require vernalization to induce flowering, 'Snowcap' requires vernalization to begin flowering.

BRIEF DESCRIPTION OF THE PHOTOGRAPHS

Figure 1:
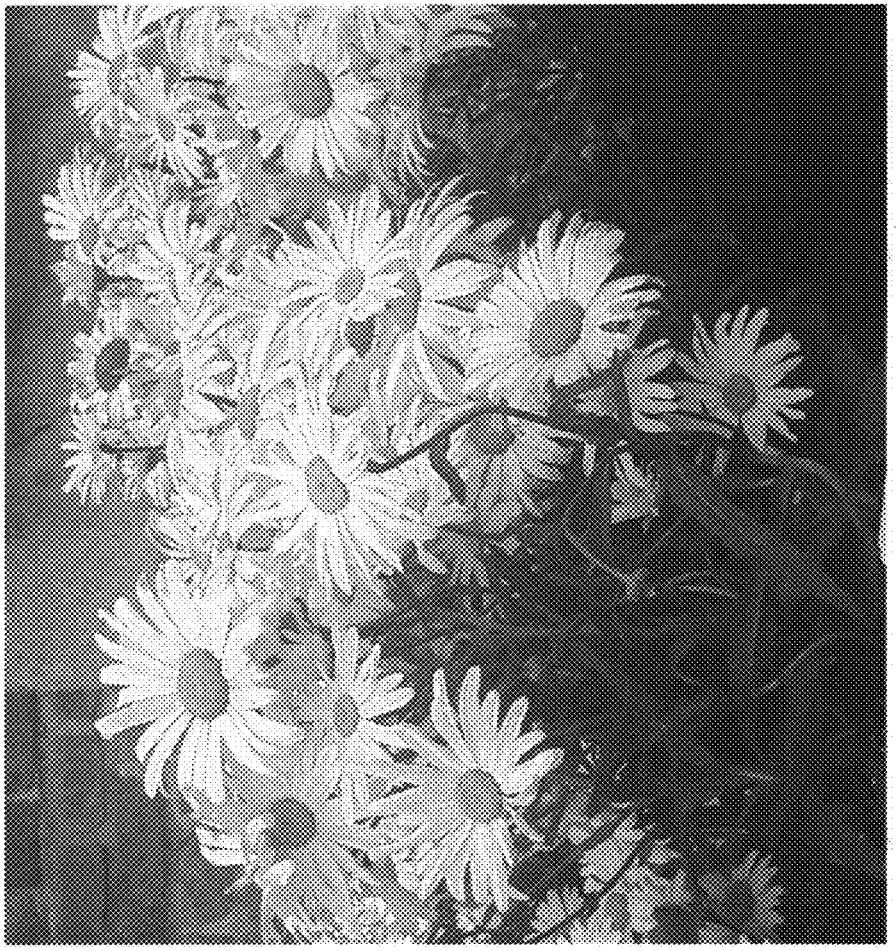

The accompanying photograph in FIG. 1 illustrates in full color a typical plant of 'DLEULUCGRC' grown in a greenhouse. The pot size is a commercial 12 cm container. The plant shown is approximately 20 weeks old.

Figure 2:
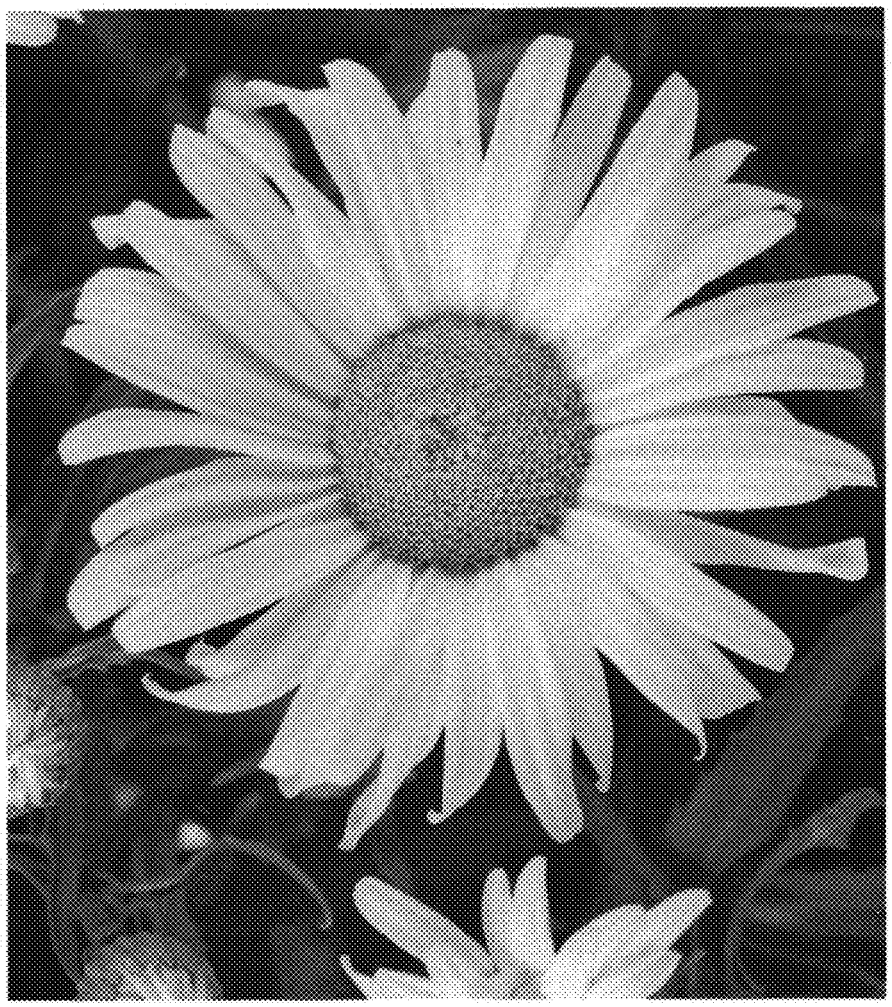

FIG. 2 illustrates a close-up view of the inflorescence.

The photographs were taken using conventional techniques and although colors may appear different from actual colors due to light reflectance it is as accurate as possible by conventional photographic techniques.

DETAILED BOTANICAL DESCRIPTION

The following descriptions and color references, except where common dictionary terms are used, are based on the 2015 edition of The Royal Horticultural Society Colour Chart.

General growing conditions of plant described:
Greenhouse/nursery/outdoors: Outdoors.
Temperature range: About 20° C. to 35° C. during the day, about 15° C. to 25° C. night.
City and country: Moshav Mishmar Hashiva, Israel.
Time of year: Late Spring.
Chemical treatments, including growth regulators: None.
Age of plant described: Six months from a rooted cutting.
Botanical classification: *Leucanthemum superbum* 'DLEULUCGRC'.

PROPAGATION

Time to rooting: 20 days at approximately 16° C.
Root description: Strong, long woody roots with fibrous secondary roots. Roots color brown, not accurately measured with the R.H.S. chart.

PLANT

Growth habit: Upright, compact hardy flowering perennial.
Height: Approximately 60 cm.
Plant spread: Approximately 35 cm.
Branching characteristics: Abundant basal branching.
Length of branches: Approximately 30 cm.
Diameter of branches: Approximately 0.3 cm.
Texture of branches: Smooth.
Internode length: Approximately 5.0 to 5.5 cm.
Strength of lateral branches: Strong and wiry.
Color of lateral branches: Near RHS Yellow-Green 144A.
Aspect/angle of branches: Straight, approximately 15 to 25 degrees from center.
Number of leaves per lateral branch: Approximately 6 pairs.

FOLIAGE

Leaf:
*Arrangement*.—Opposite.
*Average length*.—Approximately 15 cm.
*Average width*.—Approximately 2 cm.
*Shape of blade*.—Oblanceolate.
*Lobing*.—None.
*Apex*.—Acute serration
*Base*.—Broad tapered.
*Attachment*.—Sessile.
*Margin*.—Moderately serrated.
*Texture of top surface*.—Smooth.
*Texture of bottom surface*.—Smooth.
*Appearance top surface*.—Somewhat shiny.
*Appearance bottom surface*.—Matte.
*Leaf internode length*.—Approximately 5.0 to 5.5 cm.
*Color*.—Young foliage upper side: Near RHS Green 137A. Young foliage under side: Near RHS Green 137C. Mature foliage upper side: Near RI-IS Green 137A. Mature foliage under side: Near RHS Green 137C.
*Venation*.—Type: One central running from base to tip. Venation color upper side: Near RHS Green 137A. Venation color under side: Near RHS Green 137C.
*Petiole*.—None.

FLOWER

Bud:
*Bud shape*.—Slightly flattened globular.
*Bud height*.—Approximately 0.5 cm.
*Bud diameter*.—Approximately 1 cm.

Inflorescence:
*Form*.—Single, daisy-type inflorescence form with oblanceolate-shaped ray florets. Inflorescences positioned above and beyond the foliage; inflorescences terminal and axillary. Disc and ray florets developing acropetally on a capitulum. Inflorescences face mostly upright to outward.
Flower:
*Diameter of entire flower*.—Approximately 8 cm.
*Depth of flower*.—Approximately 0.8 cm.
*Width of disc*.—Approximately 2.25 to 2.5 cm.
*Depth of disc*.—Approximately 0.5 cm.
Ray florets:
*Number of ray florets*.—Average range 24 to 36.
*Length*.—Approximately 2.5 cm.
*Width*.—Approximately 0.5 cm.
*Apex shape*.—Rounded.
*Margin*.—Smooth.
*Color*.—Upper surface at first opening,. Near RHS White 155C. Upper surface at maturity: Near RHS White 155C. Upper surface at fading: Near RHS White 155C. Under surface at first opening: Near RHS White 155C. Under surface at maturity: Near RHS White 155C. Under surface at fading: Near RHS White 155C.
Disc florets:
*Number of disc florets*.—Average range 220 to 250.
*Length*.—Approximately 0.9 cm.
*Width*.—Approximately 1 mm.
*Shape*.—Tubular.
*Margin*.—Entire.
*Color*.—At first opening: Near RHS Yellow-Green 153C. At maturity: Near RHS Yellow-Green 153C. At fading: Near RHS Yellow-Green 153C.
Receptacle:
*Shape*.—Shallow convex.
*Width*.—2.0 to 2.5 cm.
*Depth*.—3 mm.
*Color*.—Near Green 137C,
Fragrance: None.
Involucral bracts/phyllaries:
*Number*.—Approximately 20.
*Length*.—Approximately 1 cm.
*Width*.—Approximately 0.3 cm.
*Shape*.—Narrow, elongated deltate.
*Texture*.—Smooth all surfaces.
*Apex shape*.—Acute.
*Margin*.—Smooth.
Peduncle:
*Length*.—Approximately 16 cm.
*Diameter*.—Approximately 0.3 cm.
*Angle*.—Upright.
*Color*.—Near RHS Yellow-Green 144A.
*Peduncle texture*.—Smooth.

REPRODUCTIVE ORGANS

Disc florets:
Androecium:
*Stamens*.—4.
*Anther shape*.—Cylindrical.
*Anther length*.—Approximately 0.5-1.0 mm.
*Anther color*.—Near RHS Yellow-Green 153C.
*Pollen quantity*.—Abundant.
*Pollen color*.—Near RHS Yellow 13B.

Gynoecium:

*Pistil number*.—1 per floret.

*Pistil shape*.—Two-parted.

*Pistil length*.—Approx. 0.2 cm.

*Style length*.—Approx. 0.1 cm.

*Style color*.—Near RHS Green 142A.

*Stigma shape*.—Less than 1 mm, misshapen linear.

*Stigma color*.—Too small to accurately measure with R.H.S. chart.

*Ovary diameter*.—0.1 cm.

*Ovary color*.—Near RHS Green 142A.

OTHER CHARACTERISTICS

Disease resistance: Neither resistance nor susceptibility to diseases or pests has been observed in this variety to date.

Drought tolerance and cold tolerance: Hardy perennial with good heat tolerance. Hardy to at least −2° C., high temperature tolerance to at least 38° C.

Fruit/seed production: Not observed.

What is claimed is:

1. A new and distinct cultivar of *Leucanthemum* plant named 'DLEULUCGRC' as herein illustrated and described.

* * * * *